United States Patent [19]
Lichtenhan et al.

[11] Patent Number: 6,100,417
[45] Date of Patent: Aug. 8, 2000

[54] FUNCTIONALIZING OLEFIN BEARING SILSESQUIOXANES

[75] Inventors: Joseph D. Lichtenhan, San Juan Capistrano; Frank J. Feher, Costa Mesa, both of Calif.; Daravong Soulivong, Martigues, France

[73] Assignee: The United States of America as represented by the Secretary of the Air Force, Washington, D.C.

[21] Appl. No.: 09/387,682

[22] Filed: Aug. 31, 1999

[51] Int. Cl.⁷ .................................................. C07F 2/08

[52] U.S. Cl. .................. 556/460; 556/459; 556/461; 528/25; 528/37

[58] Field of Search .................. 528/25, 37; 556/460, 556/459, 461

[56] References Cited

U.S. PATENT DOCUMENTS

| | | |
|---|---|---|
| 5,412,053 | 5/1995 | Lichtenhan et al. . |
| 5,484,867 | 1/1996 | Lichtenhan et al. . |
| 5,589,562 | 12/1996 | Lichtenhan et al. ................ 556/460 X |
| 5,939,576 | 8/1999 | Lichtenhan et al. .................... 556/460 |
| 5,942,638 | 8/1999 | Lichtenhan et al. .................... 556/460 |

*Primary Examiner*—Paul F. Shaver
*Attorney, Agent, or Firm*—Thomas C. Stover

[57] ABSTRACT

Method is provided for reacting silsesquioxane resins or polyhedral oligomeric silsesquioxanes (POSS) bearing one or more olefinic groups with strong acids to cleave one or more olefin bonds of the olefinic groups to form POSS species of monomers or polymers having one or more functionalities suitable for reaction with a wide range of polymeric systems, to thus form new POSS derived compounds. Also provided are the new compounds so formed.

20 Claims, No Drawings

FUNCTIONALIZING OLEFIN BEARING SILSESQUIOXANES

CROSS REFERENCE TO RELATED APPLICATIONS

This Application relates to patent applications Ser. Nos. 09/003,083, METHOD OF FUNCTIONALIZING POLYCYCLIC SILICONES AND THE RESULTING COMPOUNDS, (now U.S. Pat. No. 5,942,638); Ser. No. 09/003,084, METHOD OF FUNCTIONALIZING POLYCYCLIC SILICONES AND THE COMPOUNDS SO FORMED now U.S. Pat. No. 5,939,576; Ser. No. 09/258,248 MODIFYING POSS COMPOUNDS and Ser. No. 09/258,249, ALTERING OF POSS RINGS; all by J. D. Lichtenhan et al.

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to functionalizing of olefin bearing silsesquioxanes including POSS compounds, particularly altering or manipulating olefin groups attached to such compounds

2. Description of Related Art

Silsesquioxanes bearing olefinic groups are of interest because they are among the lowest-cost silsesquioxanes and if such groups could be converted to other functionalities, the resulting POSS derivatives might find use in a wide range of polymer systems. However, there is no suggestion of the above conversion to such derivatives in the prior art.

Also, there are teachings of the preparation of certain POSS derivatives in the above cited 4 patent applications by J. D. Lichtenhan et al. These references, however, do not suggest the above conversion.

Accordingly there is need and market for a method for cleaving olefin, or vinyl, substitutents on POSS molecules that overcomes the above prior art shortcomings.

There has now been discovered methods that rapidly and effectively cleave the vinyl bond of POSS substitutents to produce species that can be subsequently converted to various functionalized POSS compounds. That is, the invention provides efficient methods for the selective cleaving of the above vinyl substituents, using the novel process steps discussed below.

SUMMARY OF THE INVENTION

Broadly the present invention provides a method for selectively derivitizing silsesquioxane resins and polyhedral oligomeric silsesquioxanes (POSS) bearing one or more olefinic groups. That is, the invention provides a method for forming silsesquioxane derivatives comprising reacting acid to add across one or more olefinic bonds, including C=C bonds, of vinyl-containing compounds selected from the group of silsesquioxane monomeric and polymeric systems to add one or more functionalities thereto wherein the acid is selected from the group of $CF_3SO_3H$, $ClSO_3H$, $CH_3SO_3H$, $H_2SO_4$, and combinations thereof.

The invention also provides a method for forming polyhedral oligomeric silsesquioxanes (POSS) derivatives comprising reacting POSS bearing one or more vinyl groups with acid to form POSS species bearing one or more functionalites, of the formula $R_{(4-12)-x}(vinyl)_x Si_{4-12} O_{6-18}$, where R is aliphatic, aromatic, olefinic, alkoxy, siloxy or H, x is 1–12 and the acid is as stated above.

Also provided are the silsesquioxanes, including POSS, species formed by the above inventive methods.

The method of the invention includes reacting silsesquioxane resins and polyhedral oligomeric silsesquioxanes (POSS) bearing one or more olefinic groups with strong acids to ultimately form silsesquioxane and POSS species bearing one or more functionalities suitable for reaction with a wide range of polymeric systems or:

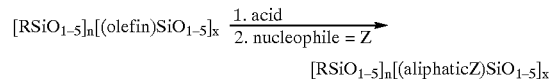

or in a related process of the of the invention:

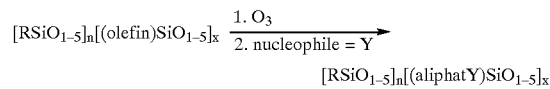

where R & x are as given above, n=4–14, aliphat is aliphatic, Z is as defined below and where Y is alcohol, acid, aldehyde and ester and where, when olefin is vinyl, aliphatic Y is silanol OH.

In the above first process, the acid adds across the double or triple bond on the olefin and is then displaced by the nucleophile to form a new silsesquioxane species bearing an aliphatic as shown, containing the nucleophile (Z).

In the above second process, the ozone oxidatively cleaves the silicon vinyl bond to form a new silsesquioxane species bearing a silanol OH in the case of vinyl or an aliphatic Y group including an aldehyde, acid or ester in the case of olefins larger than vinyl.

By "strong acid", as used herein, is meant one with a pKa number ranging from −7 to 5 and is inclusive of superacids which cannot be assigned pKa values but which are characterized by Hammett acidity values $H_0$ that range from 30 to 2.0 with the preferred range being 8–16.

By "method", as used herein, is meant "process" and vice versa.

Polyhedral oligomeric silsesquioxanes (POSS) have recently attracted widespread interest as building blocks for hybrid inorganic/organic materials. Many families of POSS monomers are now known, but some of the most promising monomers are cube-octameric frameworks with a single polymerizable pendant group.

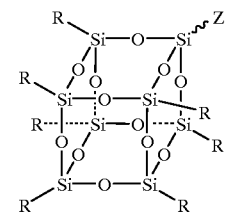

Z = polymerizable or graftable reactive group
(e.g., alcohol, epoxy, amine, acrylic, ester, olefin)

where Z is as stated above and includes water.

The above POSS derivative is a product example of the above two reactions. However cage sizes can vary as indicated in these reactions.

As part of a general effort to identify cost-effective ways for manufacturing POSS monomers, methods have been explored for preparing POSS monomers from inexpensive $R_{6-x}(vinyl)_xSi_6O_9$, $R_{8-x}(vinyl)_xSi_8O_{12}$, $R_{10-x}(vinyl)_xSi_{10}O_{15}$, $R_{12-x}(vinyl)_xSi_{12}O_{18}$, and higher silicon content monomeric frameworks and similarly from polymeric resins represented by the formula $[(RSiO_{1.5})_n(olefinSiO_{1.5})_x]_{Mwt}$ where molecular weights range from 1000 to 1,000,000 amu and where x=1–10,000. Such silsesquioxane species must contain at least one or more vinyl groups and in conjunction can contain additional organic functionalities where R=H, linear olefins (i.e. vinyl, allyl, acetylene etc.), cyclic olefins (i.e. cyclopentene, cyclohexene, cyclooctene), linear hydrocarbons (i.e. ethyl, propyl, isopropyl, butyl etc. ), cyclic hydrocarbons (i.e. cyclopropyl, cyclobutyl, cyclopentyl, cyclohexyl etc.), aromatic hydrocarbons (phenyl, tolyl, biphenyl etc.). Representative examples of low-cost vinyl containing monomeric $R_8Si_8O_{12}$ and polymeric $(RSiO_{1.5})_n$ feedstocks for utilization in processes 1 and 2 of this disclosure are shown below.

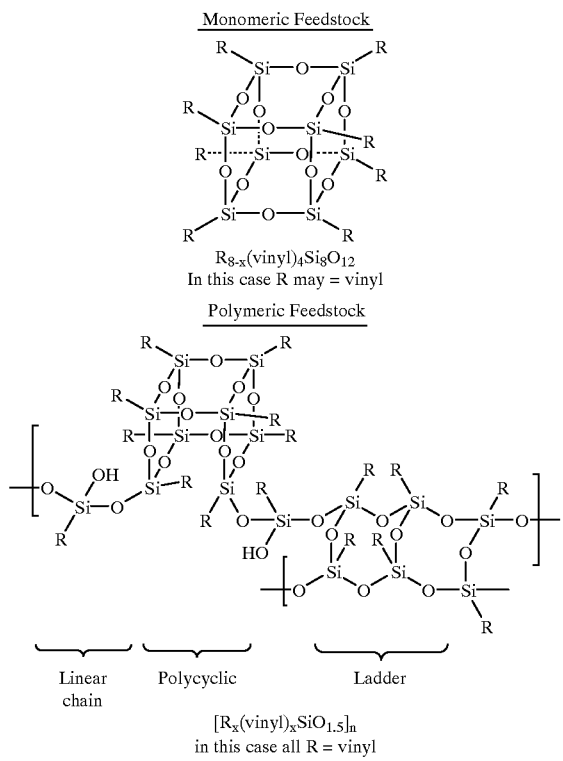

where R and x are as given above and n is 1–10,000.

As indicated, the present invention teaches two processes that enables the selective manipulation vinyl groups attached to the silicon atoms contained in monomeric and polymeric polyhedral oligomeric silsesquioxanes (POSS). Both processes yield new and desirable polyhedral oligomeric silsesquioxane chemical species.

Vinyl Group Functionalization Processes

Note both processes produce silsesquioxane products that while different are each distinctly desirable for the preparation of graftable POSS reagents, polymerizable POSS monomers or functionalized POSS-polymeric resins.

Process 1 teaches the reaction of triflic acid (TfOH) with the vinyl group of vinylsilsesquioxanes (e.g. $(vinyl)_8Si_8O_{12}$) to produce $(TfOCH_2CH_2)(vinyl)_7Si_8O_{12}$. In such a process the triflic acid adds across the vinyl group's C=C to produce an isolable intermediate species $(TfOCH_2CH_2)(vinyl)_7Si_8O_{12}$ that can be further derivitized via common nucleophilic processes such as hydrolysis to afford highly useful compounds such as $(HOCH_2CH_2)(vinyl)_7Si_8O_{12}$.

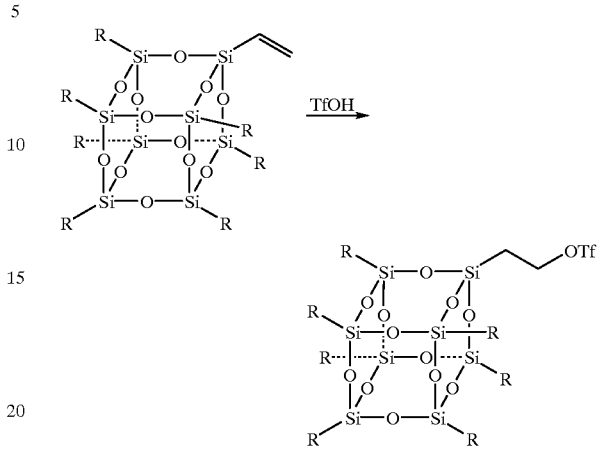

The reaction of vinyl silsesquioxanes such as $Vi_8Si_8O_{12}$ and 1 equivalent of TfOH occurs quickly upon mixing at room temperature to afford a the new silsesquioxane product $(TfOCH_2CH_2)(vinyl)_7Si_8O_{12}$ in approximately 45% yield. Based on the known reactivity of $R_8Si_8O_{12}$ frameworks toward TfOH and the tendency of some vinylsilanes to undergo protodesilylation, we expected to observe cleavage of Si—O—Si linkages and/or Si—C bonds. However this was not observed to be the case and addition of the triflate group across the C=C bond was observed and confirmed by multinuclear NMR data ($^1H$, $^{13}C$, $^{29}Si$, $^{19}F$)

The resulting triflic acid silsesquioxane intermediates can be subsequently converted into a wide variety of other functionalized silsesquioxanes. Such a transformation is of common knowledge within the field of organic chemistry and involves the displacement of the triflate group via nucleophiles such as: the hydroxyl (OH) group from water, an alkoxide (OR) group from an alcohol, carbon groups from alkaline or alkaline earth, or cuprate organics. amines from amide, and phosphorous from alkaline or alkaline earth phosphorous compounds.

The hydrolytic conversion of a POSS-triflate into a POSS-alcohol is shown below.

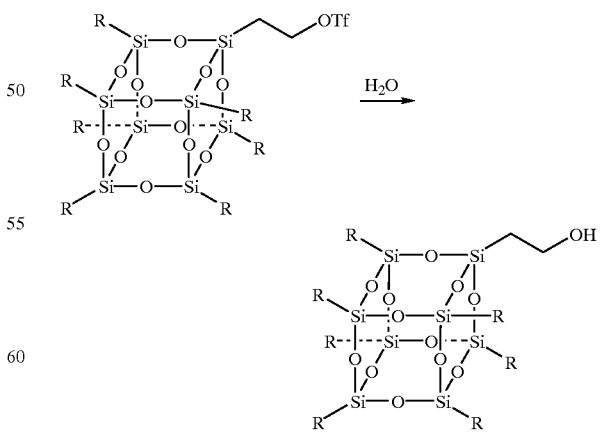

Process 2 teaches the reaction of ozone with the vinyl group of vinylsilsesquioxane (e.g. $R_{8-x}(vinyl)_xSi_8O_{12}$) to afford (e.g. $R_{8-x}(HO)_xSi_8O_{12}$) species. The ozonolysis process selectively cleaves the silicon-carbon (Si—C) of the vinyl group on molecules such as (vinyl)$_8$Si$_8$O$_{12}$ to selectively affords (vinyl)$_7$(HO)Si$_8$O$_{12}$. To obtain selective monocleavage is preferred that approximately 0.03 equivalents of ozone per vinyl group on the silsesquioxane starting material.

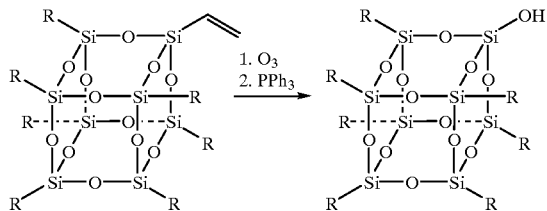

Silanol Condensation Process and Compositions

A process for the condensation of POSS monomers or resins bearing silanol (Si—OH) functionalities is shown below.

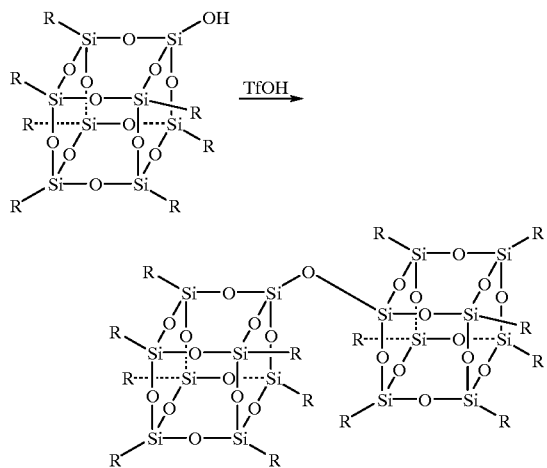

This process involves the treatment of silanol bearing silsesquioxanes with triflic acid (TfOH) to promote the condensation of two silanol groups through the net elimination of water. This process is useful for increasing the molecular weight of silsesquioxane resins and monomers to yield silsesquioxane products with improved mechanical properties and other desirable physical properties such as reduced volatility, and dimensional stability.

The following examples are intended to illustrate the invention and should not be construed in limitation thereof.

In such examples, NMR spectra were recorded on Omega-500 ($^1$H, 500 MHz; $^{13}$C, 125 MHz; $^{29}$Si, 99 MHz; $^{19}$F, 470 MHz). CHCl$_3$ and CDCl$_3$ were distilled over CaH$_2$ prior to use. All other solvents were purchased and fully purified free from oxygen and moisture prior to use.

EXAMPLES

1. Preparation of (TfOCH$_2$CH$_2$)(vinyl)$_7$Si$_8$O$_{12}$. The reaction Of Vi$_8$Si$_8$O$_{12}$ with TfOH=CF$_3$SO$_3$H occurs quickly up on mixing to afford a new silsesquioxane product in good yield (approx 45%). Triflic acid (TfOH, 1 equiv.) is added to a solution of Vi$_8$Si$_8$O$_{12}$ in CH$_2$Cl$_2$. After 3 h at 25° C., the reaction mixture was diluted with CH$_2$Cl$_2$, washed with saturated aqueous Na$_2$CO$_3$, dried over MgSO$_4$, and evaporated to afford a white solid. Analysis by $^1$H, $^{13}$C and $^{29}$Si NMR spectroscopy indicated that the crude product contains (TfOCH$_2$CH$_2$)(vinyl)$_7$Si$_8$O$_{12}$ (40–45%) and unreacted Vi$_8$Si$_8$O$_{12}$ (50%). Selected characterization data for (TfOCH$_2$CH$_2$)(vinyl)$_7$Si$_8$O$_{12}$: $_1$H NMR (500 MHz, CDCl$_3$, 25° C.): 6.25–5.75 (m, 21H), 4.75 (t, J=7 Hz, 2H, CH$_2$OTf), 1.5 (t, J=7 Hz, 2H, CH$_2$OTf). $^{13}$C{$^1$H} NMR (125 MHz, CDCl$_3$, 25° C.): 137.40, 137.24, 137.03 (3:3:1 for CH$_2$), 128.39, 128.29, 128.09 (1:3:3 for CH), 118.5 (q, J=320 Hz, CF$_3$), 75.15 (CH$_2$OTf), 14.89 (SiCH$_2$). EI (70 eV, 200° C.) exact mass for M$^+$ (found): 781.9020 (781.9041).

2. Preparation of (HOCH$_2$CH$_2$)(vinyl)$_7$Si$_8$O$_{12}$. The hydrolysis of (TfOCH$_2$CH$_2$)(vinyl)$_7$Si$_8$O$_{12}$ was performed in wet acetone/CH$_2$Cl$_2$. Analysis ($^1$H, $^{13}$C, $^{29}$Si NMR) of the crude product obtained after evaporation of the solvent indicated complete conversion of SiCH$_2$CH$_2$OTf to SiCH$_2$CH$_2$OH. Flash chromatography on silica with CH$_2$Cl$_2$ quantitatively afforded (HOCH$_2$CH$_2$)(vinyl)$_7$Si$_8$O$_{12}$ as a white solid. Selected characterization data for (HOCH$_2$CH$_2$)(vinyl)$_7$Si$_8$O$_{12}$: $^1$H NMR (500 MHz, CDCl$_3$, 25° C.): 6.15–5.9 (m, 21H), 3.847 (t, J=7.2 Hz, 2H, CH$_2$OH), 1.180 (t, J=7.2 Hz, 2H, SiCH$_2$). $^{13}$C{$^1$H} NMR (125 MHz, CDCl$_3$, 25° C.): 137.07, 137.05, 136.95 (3:3:1 for CH$_2$), 128.58, 128.56 (4:3 for CH), 58.48 (CH$_2$OH), 17.28 (SiCH$_2$). EI (70 eV, 200° C.) exact mass for M$^+$ (found): 649.9528 (649.9520).

3. Preparation of (HO)(vinyl)$_7$Si$_8$O$_{12}$. To a solution Of [(CH$_2$=CH)$_8$Si$_8$O$_{12}$] (5.400 g, 8.50 mmol) in THF (300 mL) at −78° C. was transferred a saturated solution of ozone in CH$_2$Cl$_2$ at −78° C. (0.04 M, 53 mL, 2.10 mmol). After stirring for 5 minutes, nitrogen gas was bubbled into the mixture and solid PPh$_3$ (0.671 g, 2.60 mmol) was added. The mixture was allowed to warm to room temperature and the volume of solvent was then reduced to ca. 10 mL. Addition of acetone affords the precipitation of [(CH$_2$=CH)$_8$Si$_{812}$] (4.217 g, 6.66 mmol). Evaporation of the filtrate and purification of the residue by chromatography (short flash column Of SiO$_2$) using a mixture of hexanes/CH$_2$Cl$_2$ (6:4) then CH$_2$Cl$_2$ yielded [(CH$_2$=CH)$_8$Si$_8$O$_{12}$] (0.661 g, 1.04 mmol) and (HO)(vinyl)$_7$Si$_8$O$_{12}$ (0.092 g, 0.147 mmol)respectively. $^1$H NMR (500 MHz, CDCl$_3$, 25° C.): 6.15–5.89 (m, CH=CH$_2$ ) C{$^1$H} NMR (125 MHz, CDCl$_3$, 25° C.): 137.27, 137.10, 137.06 (s for CH$_2$, 3:4:1), 128.49, 128.41, 128.26 (s for CH, 1:3:4). $^{29}$Si{$^1$H} NMR (99 MHz, CDCl$_3$, 25° C.): −79.65, −80.18 (s, 3:4), −100.86 (SiOH).

4. Preparation Of (HO)(c-C$_6$H$_{11}$)$_7$Si$_8$O$_{12}$. Ozonized oxygen gas was passed through a solution of (c-C$_6$H$_{11}$)$_7$(vinyl)Si$_8$O$_{12}$ (102 mg, 0.100 mmol) in CH$_2$Cl$_2$ (8 mL) at −78° C. until the blue color of unreacted ozone was noticeable. After stirring for 5 minutes, the solution was allo wed to warm to −20° C. and dry nitrogen was bubbled for 5 minutes. Triphenylphosphine (33 mg, 0.126 mmol) was added to the mixture, and the solution was allowed to warm to room temperature. After evaporating the solvent, the residue was redissolved in CHCl$_3$ and sodium carbonate (55 mg) was added. The mixture was heated at 60° C. for 1 hour. Then precipitation from a mixture of CHCl$_3$/CH$_3$CN affords (HO)(c-C$_6$H$_{11}$)$_7$Si$_8$O$_{12}$ as a white solid (70 mg, 69%). $_1$H NMR (500 MHz, CDCl$_3$, 25° C.): 2.40 (br s, 1H, SiOH), 1.72 (br m, 35H), 1.23 (br m, 35H), 0.76 (br m, 7H) C{$^1$H} NMR (125 MHz, CDCl$_3$, 25° C.): 27.45, 27.40, 26.86, 26.77, 26.57, 26.51 (s for CH$_2$), 23.10, 23.03, 22.93 (s for CH, 1:3:4). $^{29}$Si{$^1$H} NMR (99 MHz, CDCl$_3$, 25° C.): −67.82, −68.61 (s, 4:3), −99.81 (SiOH).

5. Preparation of [(((c-C$_6$H$_{11}$)$_7$Si$_8$O$_{12}$)$_2$O]. To a solution of [(c-C$_6$H$_{11}$)$_7$Si$_8$O$_{12}$(OH)] (268.5 mg, 0.264 mmol) in CHCl$_3$ (~1 mL) was added TfOH (40.4 mg, 0.269 mmol). The formation of a second phase (TfOH/H$_2$O) was noticed after 1 hour. The mixture was stirred overnight at 25° C. and was run through a pad of SiO$_2$ using CH$_2$Cl$_2$ as eluent. After evaporating the solvent, [((c-C$_6$H$_{11}$)$_7$Si$_8$O$_{12}$)$_2$)] was purified by a short column of silica gel using hexanes as eluent (214.4 mg, 80%). $^1$H NMR (500 MHz, CDCl$_3$, 25° C.): 2.76 (br/s, 70H), 1.25 (br s, 70H), 0.78 (br m, 14H). $^{13}$C{$^1$H} NMR (125 MHz, CDCl$_3$, 25° C.): 27.51, 27.47, 26.90, 26.86, 26.64, 26.45 (CH$_2$), 23.17, 23.14, 22.85 (s for CH, 1:3:3). $^{29}$Si{$^1$H} NMR (99 MHz, CDCl$_3$, 25° C.): −67.79, −68.58 (3:4), −109.90 (O$_3$Si—O—SiO$_3$). DSC: 439° C. (exotherm). TGA: onset 319.7° C., end 511.9° C., loss of 38.9%.

Thus processes are described for the selective manipulation of vinyl groups attached to the silicon atoms contained in polyhedral oligomeric silsesquioxanes (POSS). The silsesquioxanes of preference are the precise molecular species $R_{6-x}(vinyl)_xSi_6O_9$, $R_{8-x}(vinyl)_xSi_8O_{12}$, $R_{10-x}(vinyl)_xSi_{10}O_{15}$, $R_{12-x}(vinyl)_xSi_{12}O_{18}$, and higher silicon content monomeric species and polymeric resins represented by formula $(RSiO_{1.5})_n$ where molecular weights range from 1000 to 1,000,000 amu. The processes taught in this disclosure operate specifically on vinyl groups attached to the silsesquioxane silicon atoms. However such silsesquioxane species may also contain additional organic functionalities where R=H, linear olefins (i.e. vinyl, allyl, acetylene etc.), cyclic olefins (i.e. cyclopentene, cyclohexene, cyclooctene), linear hydrocarbons (i.e. ethyl, propyl, isopropyl, butyl etc.), cyclic hydrocarbons (i.e. cyclopropyl, cyclobutyl, cyclopentyl, cyclohexyl etc.), aromatic hydrocarbons (phenyl, tolyl, biphenyl etc.).

Process 1 teaches the reaction of triflic acid (TfOH) with the vinyl group of vinylsilsesquioxane (e.g. (vinyl)$_8$Si$_8$O$_{12}$) to produce (TfOCH$_2$CH$_2$)(vinyl)$_7$Si$_8$O$_{12}$. In such a process the triflic acid adds across the vinyl group to produce an isolable intermediate species TfOCH$_2$CH$_2$)(vinyl)$_7$Si$_8$O$_{12}$ that can be further derivitized via common nucleophilic processes such as hydrolysis to afford highly useful compounds such as (HOCH$_2$CH$_2$)(vinyl)$_7$Si$_8$O$_{12}$.

Process 2 teaches the reaction of ozone with the vinyl group of vinylsilsesquioxane (e.g. $R_{8-x}(vinyl)_xSi_8O_{12}$) to afford (e.g. $R_{8-x}(HO)_xSi_8O_{12}$) species. The ozonolysis process selectively cleaves the silicon-carbon (Si—C) of the vinyl group on molecules such as (vinyl)$_8$Si$_8$O$_{12}$ and can be controlled to selectively produce highly desirable monosilanol species such as (vinyl)$_7$(HO)Si$_8$O$_{12}$.

Silsesquioxanes bearing alcohols (via process 1) or bearing silanols (via process 2) are extremely valuable for use as graftable reagents, polymerizable monomers, or functional silsesquioxane polymers.

Finally a process for the condensation of POSS monomers or resins bearing silanol (Si—OH) functionalities is also taught. This process involves the treatment of silanol bearing silsesquioxanes with triflic acid (TfOH) to promote the condensation of two silanol groups to produce Si—O—Si linkages through the net elimination of water as a by product. This process is useful for increasing the molecular weight of silsesquioxane resins, and for linking POSS monomers to yield silsesquioxane products with improved mechanical properties and other desirable physical properties such as reduced volatility, improved scratch resistance, and dimensional stability.

What is claimed is:

1. A method for forming silsesquioxane derivatives comprising reacting acid to add across one or more olefinic bonds of olefin-containing compounds selected from the group of silsesquioxane monomeric and polymeric systems to add one or more functionalities thereto wherein said acid is selected from the group of CF$_3$SO$_3$H, ClSO$_3$H, CH$_3$SO$_3$H, H$_2$SO$_4$ and combinations thereof.

2. A method for forming polyhedral oligomeric silsesquioxanes (POSS) derivatives comprising reacting POSS bearing one or more olefin groups with acid to form POSS species bearing one or more functionalites, of the formula $R_{(4-12)-x}(aliphatic\ acid)_xSi_{4-12}O_{6-18}$, where R is aliphatic, aromatic, olefinic, alkoxy, siloxy or H, x is 1–12 and said acid is selected from the group of CF$_3$SO$_3$H, ClSO$_3$H, CH$_3$SO$_3$H, H$_2$SO$_4$ and combinations thereof.

3. The method of claim 2 wherein said POSS species is reacted with said acid and then a nucleophile to form a POSS derivative given by:

$$[RSiO_{1-5}]_n[(olefin)SiO_{1-5}]_x \xrightarrow[\text{2. nucleophile = Z}]{\text{1. acid}}$$

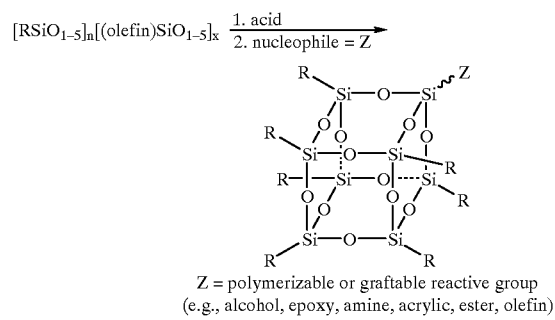

Z = polymerizable or graftable reactive group
(e.g., alcohol, epoxy, amine, acrylic, ester, olefin)

where Z is as given above or water and n is 4–14.

4. The method of claim 2 wherein said POSS species is reacted with said acid and then a nucleophile to form a POSS derivative given by:

$$[RSiO_{1-5}]_n[(olefin)SiO_{1-5}]_x \xrightarrow[\text{2. nucleophile = Z}]{\text{1. acid}}$$

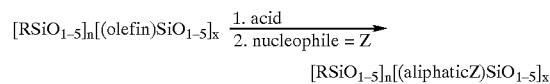

$[RSiO_{1-5}]_n[(aliphaticZ)SiO_{1-5}]_x$ where Z is alcohol, epoxy, amine, acrylic, ester, isocyanate, strained cyclic olefin or water and n is 4–14.

5. The method of claim 2 wherein said POSS species is reacted with ozone and then a nucleophile to form a POSS derivative given by:

$$[RSiO_{1-5}]_n[(olefin)SiO_{1-5}]_x \xrightarrow[\text{2. nucleophile = Y}]{\text{1. O}_3}$$

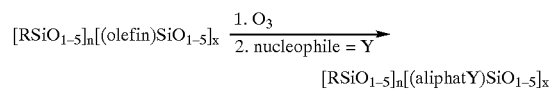

$[RSiO_{1-5}]_n[(aliphatY)SiO_{1-5}]_x$ where n is 4–14, aliphat is aliphatic, Y is alcohol, acid, aldehyde or ester and where, when olfin is vinyl, Y is silanol OH.

6. The method of claim 2 wherein:

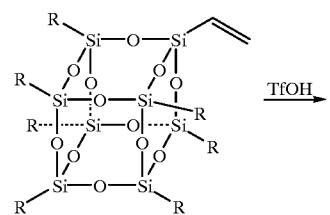

-continued

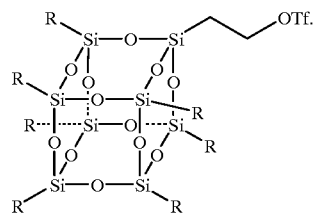

7. The method of claim 6 wherein:

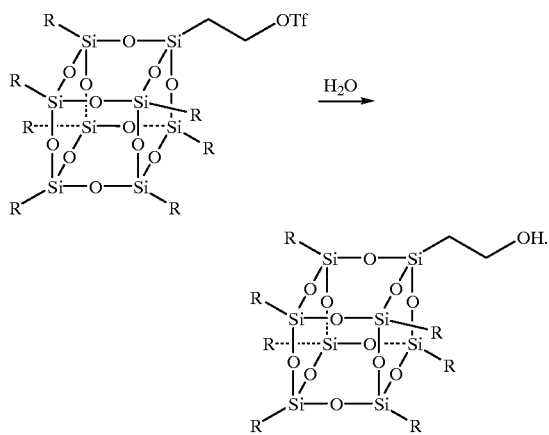

8. The method of claim 5 wherein:

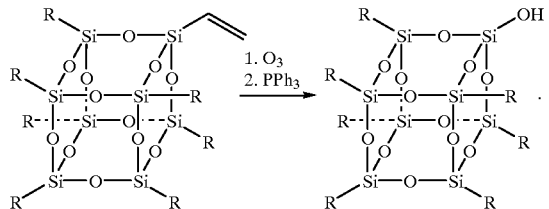

9. The method of claim 8 wherein:

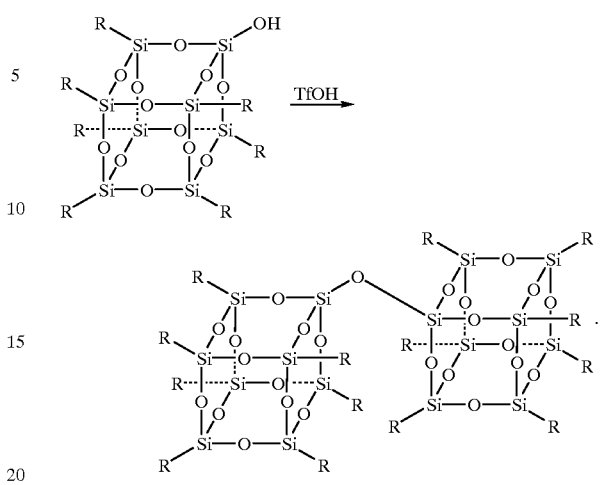

10. A POSS derivative comprising $R_{(4-12)-x}(vinyl)_x Si_{4-12} O_{6-18}$, where x is 1–12 and polymers thereof.

11. A silsesquioxane derivative made by the process of claim 1.

12. A silsesquioxane derivative made by the process of claim 2.

13. A silsesquioxane derivative made by the process of claim 3.

14. A silsesquioxane derivative made by the process of claim 4.

15. A silsesquioxane derivative made by the process of claim 5.

16. A silsesquioxane derivative made by the process of claim 6.

17. A silsesquioxane derivative made by the process of claim 7.

18. A silsesquioxane derivative made by the process of claim 8.

19. A silsesquioxane derivative made by the process of claim 9.

20. A silsesquioxane resin comprising $[R_x(vinyl)_x SiO_{1.5}]_n$ where n is 8–10,000 or more.

* * * * *